(12) United States Patent
Jordan et al.

(10) Patent No.: US 9,114,013 B2
(45) Date of Patent: Aug. 25, 2015

(54) MALAR IMPLANT WITH DUAL-PLANE ADHESION

(71) Applicants: J. Randall Jordan, Madison, MS (US); Benjamin Googe, Jackson, MS (US)

(72) Inventors: J. Randall Jordan, Madison, MS (US); Benjamin Googe, Jackson, MS (US)

( * ) Notice: Subject to any disclaimer, the term of this patent is extended or adjusted under 35 U.S.C. 154(b) by 0 days.

(21) Appl. No.: 14/163,184

(22) Filed: Jan. 24, 2014

(65) Prior Publication Data

US 2015/0209147 A1 Jul. 30, 2015

(51) Int. Cl.
*A61F 2/02* (2006.01)
*A61F 2/28* (2006.01)
*A61F 2/00* (2006.01)

(52) U.S. Cl.
CPC ............. *A61F 2/2875* (2013.01); *A61F 2/0059* (2013.01); *A61F 2002/2882* (2013.01)

(58) Field of Classification Search
CPC ................ A61F 2/0059; A61F 2/2875; A61F 2002/2882; A61F 2002/2878
See application file for complete search history.

(56) References Cited

U.S. PATENT DOCUMENTS

| | | | |
|---|---|---|---|
| 4,790,849 A | 12/1988 | Terino | |
| 4,969,901 A * | 11/1990 | Binder | 623/17.18 |
| 5,069,660 A | 12/1991 | Grantham | |
| 5,139,497 A | 8/1992 | Tilghman et al. | |
| 5,380,329 A | 1/1995 | Elia et al. | |
| 5,421,831 A | 6/1995 | Giampapa | |
| 5,496,371 A | 3/1996 | Eppley et al. | |
| 5,514,179 A | 5/1996 | Brennan | |
| 5,876,447 A | 3/1999 | Arnett | |
| 6,277,150 B1 | 8/2001 | Crawley et al. | |
| 6,485,503 B2 | 11/2002 | Jacobs et al. | |
| 6,645,226 B1 * | 11/2003 | Jacobs et al. | 606/215 |
| 7,887,587 B2 | 2/2011 | Griffiths et al. | |
| 8,097,041 B2 | 1/2012 | Barbosa | |
| 2002/0022883 A1 * | 2/2002 | Burg | 623/8 |
| 2006/0217813 A1 * | 9/2006 | Posnick et al. | 623/17.18 |
| 2009/0082791 A1 | 3/2009 | Schroeder et al. | |
| 2010/0234947 A1 | 9/2010 | Ben Rubi et al. | |
| 2011/0264138 A1 | 10/2011 | Avelar et al. | |
| 2015/0105858 A1 * | 4/2015 | Papay et al. | 623/11.11 |

OTHER PUBLICATIONS

Niamtu III, Joe, "Malar and Submalar Implants," Internet. Available at http://www.lovethatface.com/cosmetic-facial-surgery-richmond-va/midface-procedures/cheek-implants/. Last visited Oct. 27, 2013, and believed to be prior art.

* cited by examiner

*Primary Examiner* — Thomas J Sweet
*Assistant Examiner* — Daniel Bissing
(74) *Attorney, Agent, or Firm* — PatentBest; Andrew McAleavey

(57) ABSTRACT

A malar implant for mid-face lifts and reconstructions is disclosed. The malar implant is designed to be attached to both bone and soft tissue, and provides both volume and soft tissue lift. A depending tab or lip on the superior edge of the implant attaches to the inferior orbital rim. The implant has a central plateau, which may be gently curved, that includes a number of soft tissue spikes. In one embodiment, the soft tissue spikes have the general shapes of bent isosceles triangular pyramids, thicker at the base than at the tip. The soft tissue spikes may be angled upwardly, toward the superior edge, to reposition and suspend the soft tissues of the mid-face.

14 Claims, 6 Drawing Sheets

020
MALAR IMPLANT WITH DUAL-PLANE ADHESION

BACKGROUND OF THE INVENTION

1. Field of the Invention

In general, the invention relates to surgical implants, and in particular to a malar implant with dual-plane adhesion.

2. Description of Related Art

The malar fat pads lie just under the skin of the cheeks, over the zygomatic bones and maxilla, and give definition to the cheeks. In a young face, the prominence, position, and volume of the malar fat pads provide much of the classic "youthful" facial appearance. As the face ages, the malar fat pads lose both elasticity and tissue, and the effects of gravity cause them to descend. Aging also causes changes in the underlying bone, and ultimately, a significant difference in the appearance of the mid-face.

Mid-face lifts are surgical procedures used to restore the youthful appearance of the face by, among other things, resetting the position of the malar fat pads. Traditionally, this has been done endoscopically, by making a number of small incisions in the face, dissecting the facial tissue subperiosteally, and placing sutures strategically to tighten and lift the face. The malar fat pad is generally fastened to the temporalis fascia.

A newer method, called a ribbon lift, is also used. In a ribbon lift, the face may be dissected endoscopically, as described above, or an incision may be made less invasively behind the lower eyelid. A device that has a spiked or tined portion and a connected ribbon portion is inserted into the incision and moved under the malar fat pad. The spiked or tined portion adheres to the tissue of the malar fat pad, and the elongated ribbon connected to it allows the surgeon to pull the malar fat pad into a more desirable position. The surgeon then secures the ribbon in place. The ENDOTINE® MID-FACE ST (MicroAire, Inc., Charlottesville, Va., United States) is one of the better-known mid-face ribbon-type implants. The principles of implants with spikes for soft tissue are described in U.S. Pat. Nos. 6,645,226 and 6,485,503, both of which are incorporated by reference in their entireties. While the ENDOTINE® MID-FACE ST does reposition the soft tissue, it does not add any additional volume to the underlying structures of the mid-face—any appearance of additional volume is created by repositioning the soft tissue.

There are also implants that are intended to add volume to the cheeks. U.S. Pat. No. 4,790,849, which is incorporated by reference, is one early example of this. The MEDPOR® cheek implant (Stryker Corporation, Kalamazoo, Mich., United States) is currently one of the more popular devices. These kinds of implants are not typically secured to the bones, but may adhere to the soft tissue, and do not reposition or suspend the soft tissue of the mid-face.

SUMMARY OF THE INVENTION

One aspect of the invention relates to a malar implant. The malar implant is made of a biocompatible polymer, is generally four-sided, and is contoured to follow the curvature of the zygomatic bone and maxilla. The malar implant includes a raised central plateau on which are installed a number of soft tissue spikes. A superior side edge of the malar implant is contoured to fit around the orbital rim, and a tab or lip extends outwardly and at an angle and allows the malar implant to be secured to the inferior orbital rim.

The malar implant and its central plateau provide volume when the malar implant is used in a mid-face lift procedure. Additionally, the soft tissue spikes adhere to the tissue of the malar fat pad and can be used to reposition and lift it. Thus, the malar implant provides both volume and lift while adhering to both bone and soft tissue. Additionally, the implant allows tissue to be repositioned and lifted in vectors other than the purely vertical. Malar implants according to this aspect of the invention may be made in a variety of different sizes, widths, and thicknesses in order to accommodate different patient skull morphologies, different degrees of facial volume and lift, and other factors.

Another aspect of the invention relates to soft tissue spikes for biocompatible surgical implants. The soft tissue spikes have the general shape of an isosceles triangular pyramid, wider at the base and tapered toward the tip. The tips of the soft tissue spikes are hooked such that the tips make a first angle with respect to the central axes of their respective soft tissue spikes, with the outermost extent of each spike being relatively bulbous. The soft tissue spikes may also be inclined, such that their central axes make defined angles with respect to normals to the surface or device on which they are installed.

Yet another aspect of the invention relates to procedures for placing malar implants. Generally speaking, these procedures involve securing a malar implant, such as the one described above, to the inferior orbital rim of the skull, repositioning the soft tissues of the mid-face in a desired position, and engaging the soft tissues with the soft tissue spikes of the malar implant to retain them in the desired position.

These and other aspects, features, and advantages of the invention will be set forth in the description that follows.

BRIEF DESCRIPTION OF THE DRAWING FIGURES

The invention will be described with respect to the following drawing figures, in which like numerals are used to represent like features, and in which.

DETAILED DESCRIPTION

Figure 1:
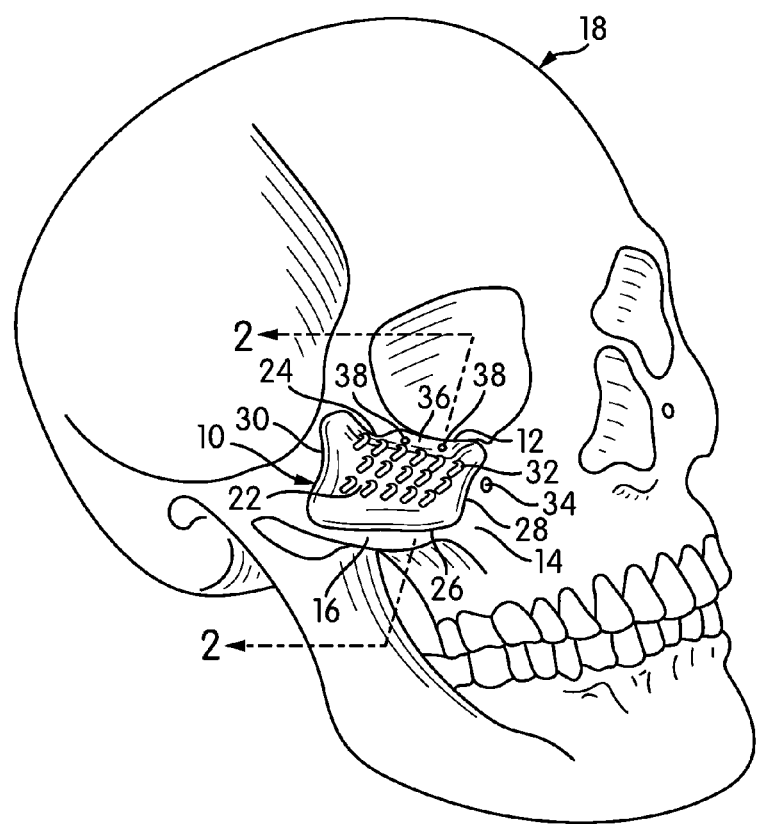
FIG. 1 is a side perspective view of a malar implant according to one embodiment of the present invention, shown as attached to the maxilla and zygomatic bone to illustrate its position, but without soft tissues illustrated.
Figure 2:
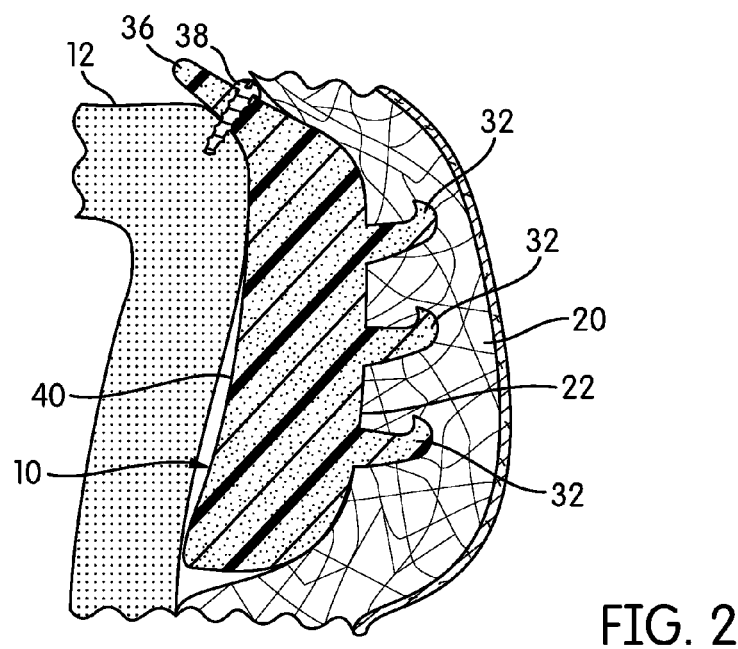
FIG. 2 is a schematic cross-sectional view of the malar implant, taken along Line 2-2 of FIG. 1, showing the implant as positioned within the mid-face, illustrating the malar implant in position adhered to both the bone and the malar fat pad.
Figure 3:
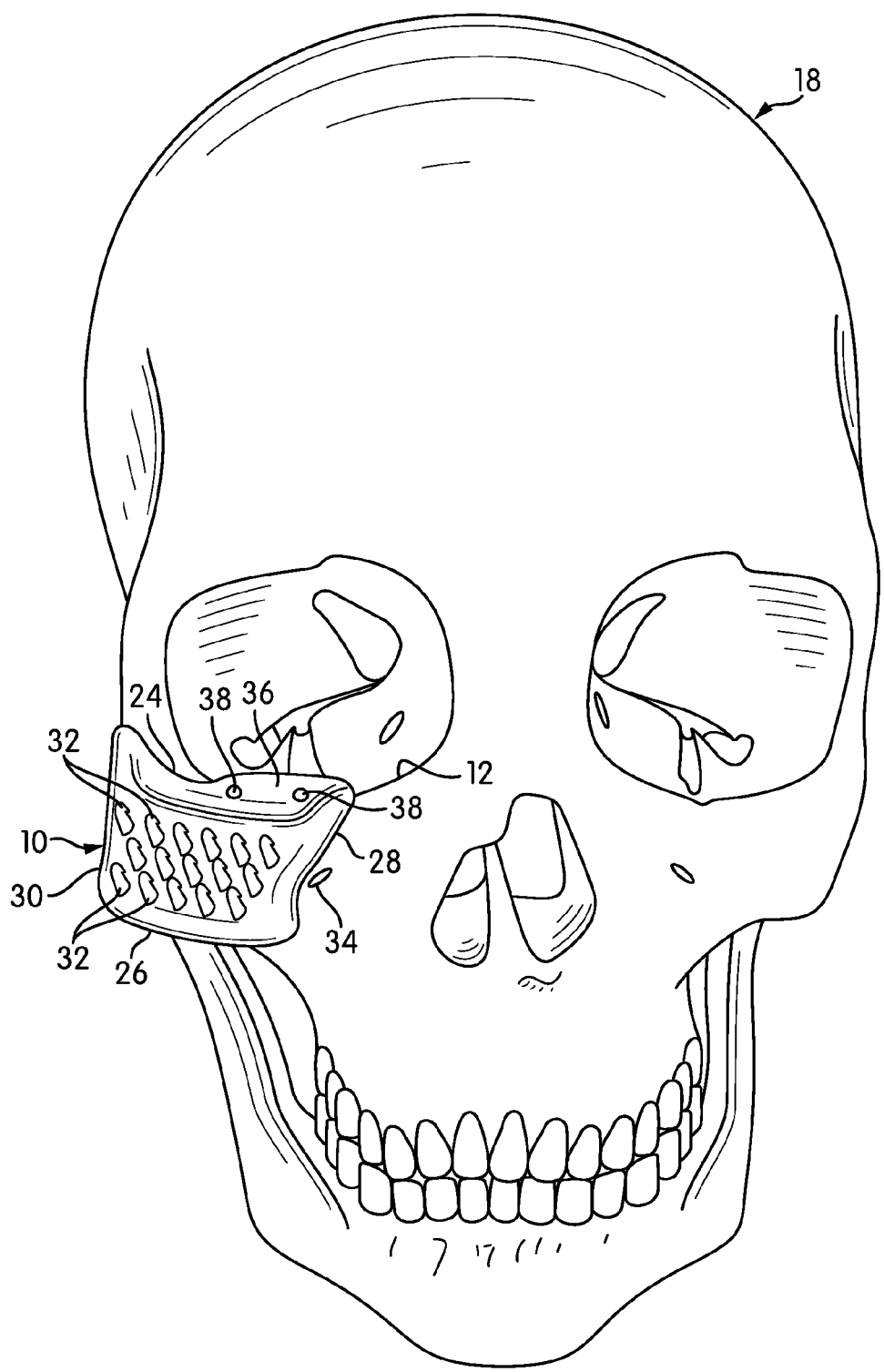
FIG. 3 is a front perspective view of the implant of FIG. 1, shown as attached to the maxilla and zygomatic bone, but without soft tissues illustrated.

FIG. 1 is a side perspective view of a malar implant, generally indicated at 10, shown as installed along the inferior orbital rim 12 and extending along the maxilla 14 and zygomatic bones 16 of a human skull 18, and FIG. 3 is a front perspective view of the malar implant 10, shown as installed on the skull 18. So as to emphasize the installed position of the malar implant 10 relative to the skull 18, FIGS. 1 and 3 omit the soft tissues and show only the bone. FIG. 2, by contrast, is a cross-section of the malar implant 10, taken through Line 2-2 of FIG. 1, illustrating the malar implant 10 attached to bone, in this case, the inferior orbital rim 12, as well as adhering to the soft tissue of the malar fat pad 20.

For simplicity in illustration, FIGS. 1 and 3 illustrate a malar implant 10 installed on only one side of the face, although malar implants 10 would be installed bilaterally in typical mid-face lifts. However, in cases of facial reconstruction or deformity repairs, a malar implant 10 might be used on only one side of the face. As will be described below in more detail, if malar implants 10 are used bilaterally, the surgeon may choose two malar implants 10 of slightly different sizes or characteristics, in order to best accommodate the characteristics of, and desired changes to, each side of the face. Of course, malar implants 10 with the same basic size and shape may be made in "left sided" and "right sided" variants to fit each side of the face.

Figure 4:
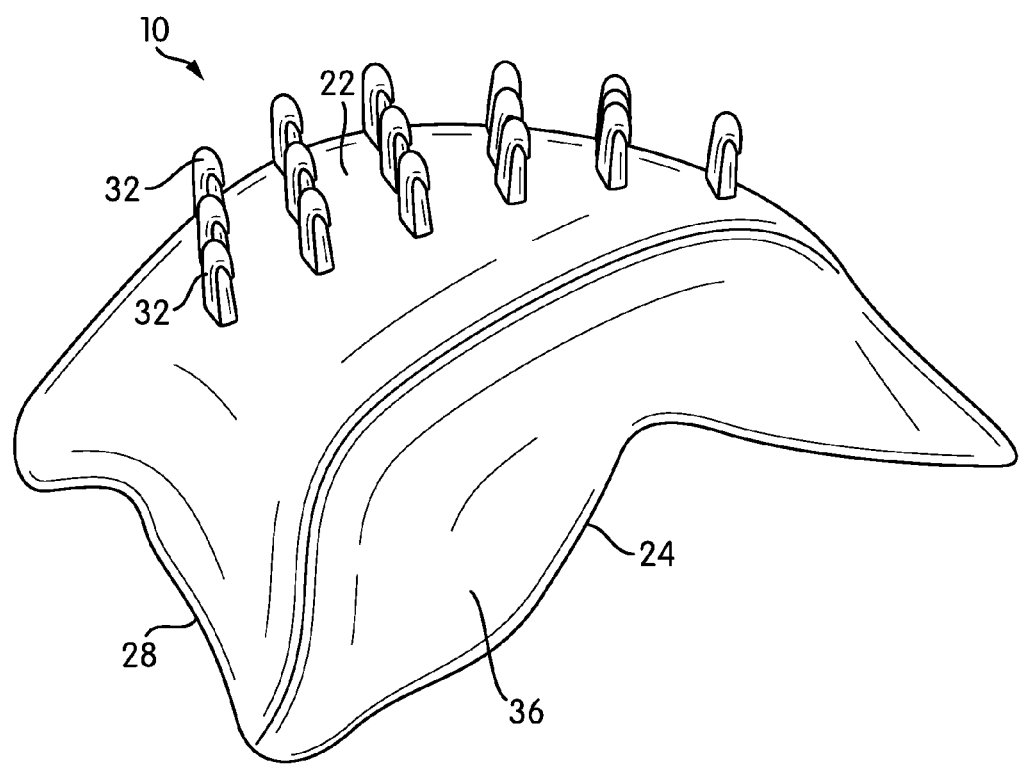
FIG. 4 is a side perspective view of the malar implant of FIG. 1 in isolation.
Figure 5:
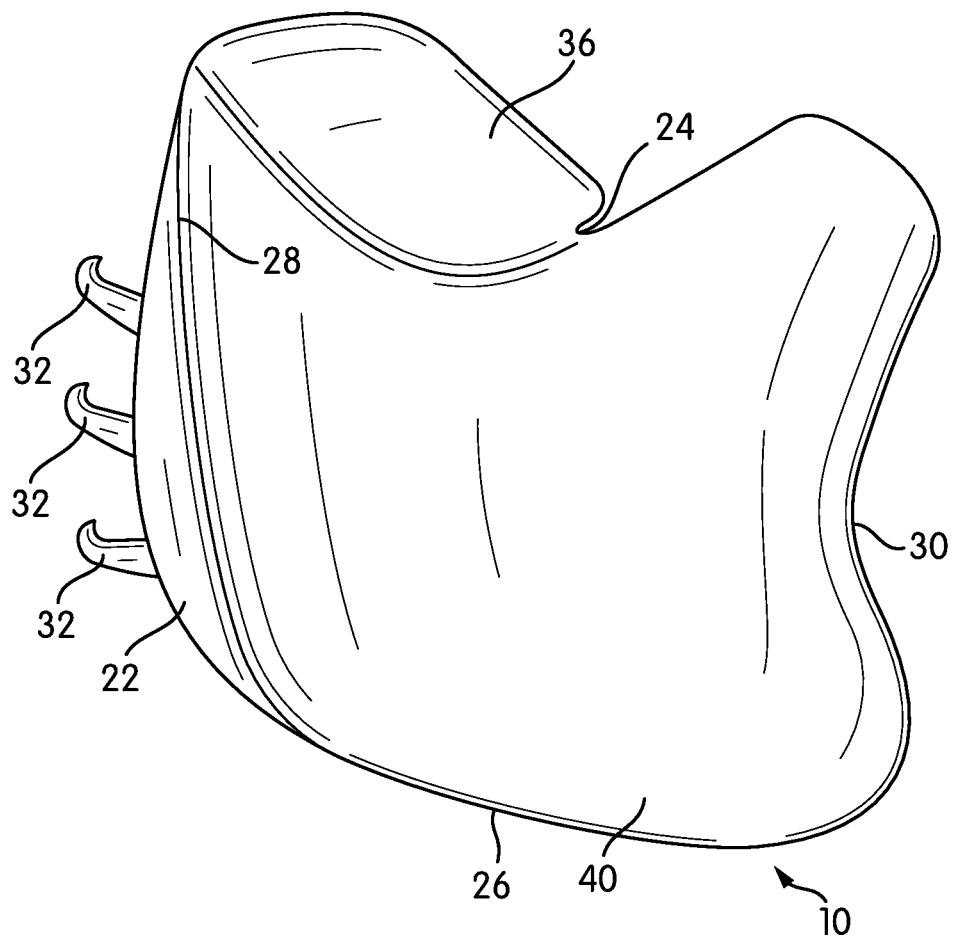
FIG. 5 is a rear perspective view of the malar implant of FIG. 1 in isolation.

As installed, the malar implant 10 provides volume to the area of the mid-face, and also repositions and holds the malar fat pad 20 in a desired location. FIG. 4 is a side perspective view of the malar implant 10, and FIG. 5 is a rear perspective view. As shown in FIGS. 1-5, the malar implant 10 generally mirrors the curvature of the zygomatic bone and maxilla. The malar implant 10 has a central, contoured plateau 22 that extends outwardly from the zygomatic bone 16 and maxilla 14 and slopes down, toward the bone, at its edges.

As can be seen in the figures, the malar implant 10 is generally four sided, and has a superior side 24, an inferior side 26, a medial side 28, and a lateral side 30. (In this description, the anatomical-directional terms "superior," "inferior," "medial," "lateral," and other such terms, are used with respect to the position of the malar implant 10 as installed on the skull 18 in the position shown in FIGS. 1 and 3.) In the illustrated embodiment, the four sides 24, 26, 28, 30 are relatively distinct, but in other embodiments, the shape may be slightly different and, for example, one side may transition into the others without sharp or defined corners between the sides.

On the central plateau 22 are a plurality of soft tissue spikes 32 that allow the malar implant 10 to adhere to and grip soft tissue, and in particular, the soft tissue of the malar fat pad 20, as can be seen in FIG. 2. These soft tissue spikes 32 extend upwardly, suspending the soft tissue against gravity and other forces that would otherwise cause them to slide downwardly. The soft tissue spikes 32 will be described below in more detail.

The sides of the malar implant 10 are shaped to accommodate the anatomical features of the skull. For example, the medial side 28 of the malar implant 10 is curved or notched inward to avoid interfering with the infraorbital foramen 34.

Along the superior side 24 of the malar implant 10, an inwardly-extending tab or lip 36 is provided. The tab or lip 36 provides room for one or more fasteners 38 to secure the malar implant 10 to the inferior orbital rim. In some embodiments, the tab or lip 36 may include holes that are pre-drilled or pre-formed for placement of fasteners 38. However, in many embodiments, the tab or lip 36 may be made of a drillable material, and the surgeon may drill the necessary holes in a place of his or her choosing. In some embodiments, for example, the tab or lip 36 may extend about 5 mm deep into the orbit, and may have a width of at least 1.5-2.0 mm, enough to accommodate one or two fasteners 38. The fastener or fasteners 38 may be resorbable in some embodiments, although in other embodiments, any small craniofacial screw or other suitable fastener may be used.

As shown particularly in FIGS. 2 and 5, the rear surface 40 of the malar implant 10 is also slightly contoured in the illustrated embodiment, and extends outwardly, such that the surface 40 is slightly cupped or concave. In general, the contour of the rear surface 40 and the shape of the malar implant 10 as a whole may be chosen to minimize any gaps between the implant 10 and the underlying bone.

Figure 6:
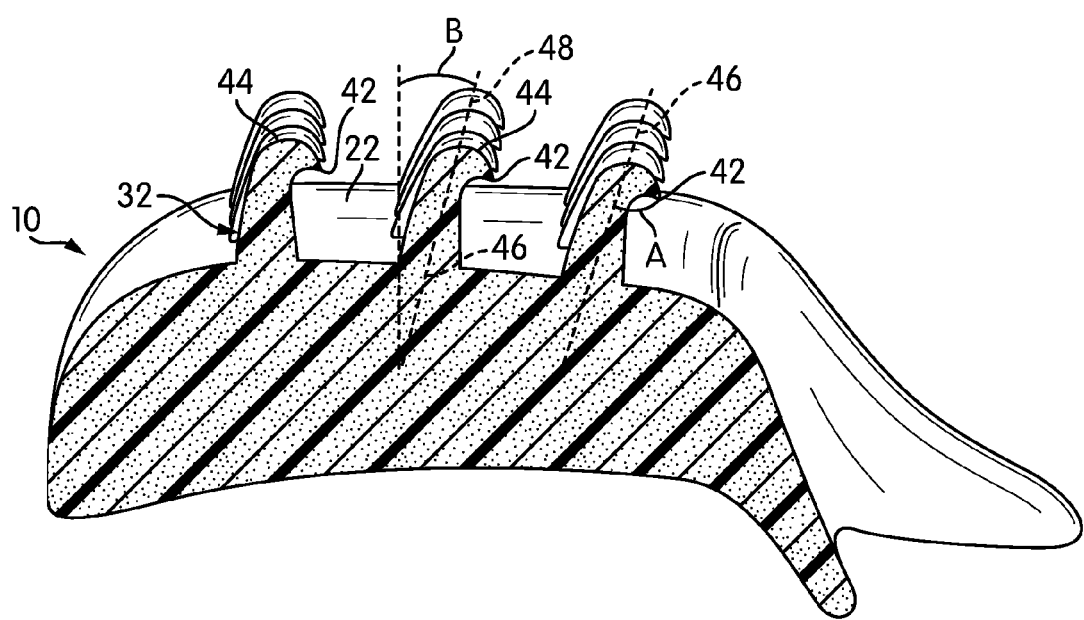
FIG. 6 is a partially sectional perspective view of the malar implant of FIG. 1, illustrating the profiles of the soft tissue spikes.

As shown in FIGS. 1-5 and in the partially cross-sectional view of FIG. 6, the illustrated embodiment of the malar implant 10 includes three offset rows of soft tissue spikes 32, with 5-6 soft tissue spikes 32 per row. The malar implant 10 may use any known type or number of soft tissue spikes, depending on the embodiment and a number of other factors. For example, soft tissue spikes like those disclosed in U.S. Pat. Nos. 6,645,226 and 6,485,503 may be used in some embodiments of the invention, and both of those patents are incorporated by reference in their entireties.

The number of soft tissue spikes 32 may vary from embodiment to embodiment. Malar implants 10 may be made in a variety of different sizes to accommodate different facial features and different degrees of augmentation, and smaller malar implants 10 may have fewer soft tissue spikes 32. For example, in a typical female patient with an average-size facial morphology and a moderate degree of desired lift, 15-20 soft tissue spikes 32 may be sufficient.

Generally speaking, each malar implant 10 should have enough soft tissue spikes 32 to provide a sufficient upward force to hold the malar fat pad in an elevated position. As those of skill in the art will appreciate, this, in turn, depends on the force necessary to lift the malar fat pads 20, as well as the mechanical properties of the soft tissue spikes 32 themselves. Additionally, while malar implants 10 may primarily be used to provide vertical lift and fixation of the malar fat pads 20, in at least some embodiments, the number and spacing of the soft tissue spikes 32 should be sufficient to allow the malar fat pads 20 and other soft tissues to be moved and fixed horizontally as well. This is one particular advantage of the malar implant 10—in addition to providing volume, the implant 10 can provide lift and fixation in a number of different vectors.

Figure 7:
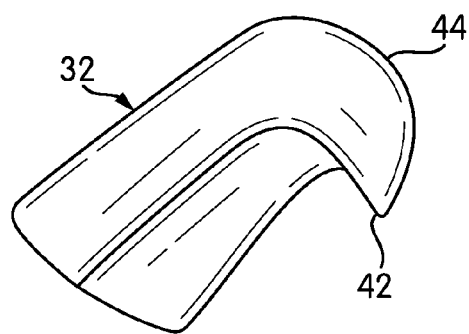
FIGS. 7-9 are perspective views of one of the soft tissue spikes from various angles.
Figure 8:
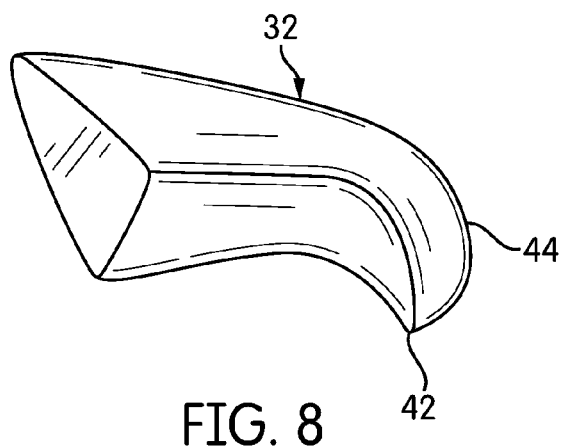
Figure 9:
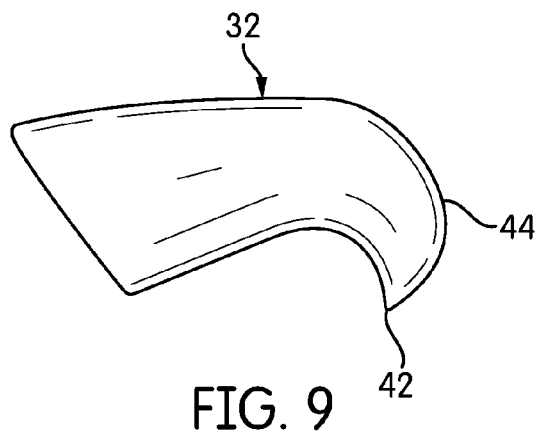

FIGS. 7-9 are perspective views of a single soft tissue spike 32 in isolation. As shown, the tissue spikes 32 have the basic form of isosceles triangular pyramids, wider at the base than at the top, with "dog-eared" or depending tips 42 that are hooked toward the base and, when installed, toward the surface of the central plateau 22. Thus, the outermost extent 44 of each tissue spike 24 is rounded and relatively bulbous, with the actual tip 32 making a first angle, illustrated as angle A in FIG. 6, of about 90° relative to a central axis 46 of the soft tissue spike, although a range of about 80-120° for angle A may be suitable in other embodiments when more or less "locking" potential is desired for secure adhesion to the soft tissue.

In the illustrated embodiment, the central axis 46 of each soft tissue spike 32 makes a second angle B, shown in FIG. 6, of about 60° with respect to the normal 48 to the central plateau 22 of the implant 10, although in other embodiments, a number of different angles may be used, for example, in the range of about 45-65°.

As shown, the malar implant 10 of the illustrated embodiment uses soft tissue spikes 32 of essentially the same length, arranged in a regular pitch with angles A and B that are the same or essentially the same for each of the tissue spikes 32. However, that need not be the case in all embodiments. With respect to tissue spike length, since the central plateau 22 of the malar implant 10 is itself curved, the soft tissue spikes 32 themselves may vary slightly in length, if desired, so that all of the soft tissue spikes 32 terminate in the same plane or along the same defined curve.

In other embodiments, patient and procedural factors like variable distribution of fat in the malar area, a mid-face lift that requires a more superficial soft tissue pulling vector, weakened soft tissue in the anchoring region, or scarring from previous surgeries might make it advantageous to space the tissue spikes 32 more irregularly, or to use soft tissue spikes 32 of varying lengths and different pitches. However, even when soft tissue spikes of different lengths are used, it may be advantageous if all of the soft tissue spikes 32 "hook" or engage in the same way, so that they engage uniformly and in response to the same type of motion.

It should also be understood that while the soft tissue spikes 32 illustrated particularly in FIGS. 7-9 are especially suitable for use with the malar implant 10, soft tissue spikes like those described and illustrated here may be used in other applications as well. For example, soft tissue spikes like soft tissue spikes 32 may be used on ribbon-type lift devices, as well as other kinds of devices.

In various embodiments of the invention, any suitable biocompatible material may be used for the malar implant 10 and its components. As shown particularly in FIGS. 2 and 6, in the illustrated embodiment, the body of the malar implant 10 and the soft tissue spikes 32 are made of the same material and are formed together, e.g., by injection molding, sintering, machining, or any other suitable process. However, in some embodiments, the soft tissue spikes 32 may be made of a different material. For example, metal soft tissue spikes 32 could be embedded in or otherwise secured to a biocompatible plastic malar implant 10 during manufacture.

One particularly suitable biocompatible material may be porous high-density polyethylene (PHDPE), such as the porous high-density polyethylene sold under the name MED-POR® (Stryker Corporation, Kalamazoo, Mich., United States). As those of skill in the art will appreciate, HDPE and PHDPE are biocompatible but not resorbable by the body; that is, they are permanent materials once implanted. In some embodiments, it may be desirable to make the malar implant 10, or just the soft tissue spikes 32, resorbable. In those embodiments, a number of known biocompatible and resorbable materials could be used, such as polylactic acid polymers, polyglycolic acid polymers, and hybrids or copolymers of polylactic acid and polyglycolic acid.

In a typical implantation procedure, the surgeon would first consult with the patient to determine the desired degree of mid-face lift and any other factors that might affect the procedure. As was noted briefly above, the malar implants 10 will generally be made in different physical sizes and in different widths and thicknesses to accommodate different skull sizes and morphologies and different degrees of desired lift. In some cases, for example, a thicker malar implant 10 (i.e., one that adds more volume) may be used to compensate for a significantly degraded malar fat pad 20. In other cases, where significant, viable soft tissue remains, a thinner implant that adds less volume may be used, with a lifted and repositioned malar fat pad 20 providing much of the desired volume. As one example, the implant may be approximately 4 cm wide, measured at its greatest extents, and approximately 2.5 cm high, with a depth of approximately 1-1.5 cm.

During the procedure, a patient would be placed under general anesthesia, and the surgeon would make an initial incision. Typically, that initial incision would be a so-called "minimally invasive" incision made behind the lower eyelid, although the surgeon may make the initial incision in other places as well. Once that is complete, the surgeon would dissect the facial tissues away from the skull down to the inferior orbital rim. A periosteal elevator, or another appropriate surgical tool, would be used to separate the periosteum from the maxilla underneath the malar fat pad. The malar implant 10 would then be inserted and positioned subperiosteally under the malar fat pad 20. The malar implant 10 would then be secured to the inferior orbital rim by drilling appropriate openings in or through the lip or tab 36 and inserting fasteners 38. The surgeon would select the degree of "lift" provided by the malar implant 10 by selecting the vertical position of the soft tissue of the cheek before driving the soft tissue spikes 32 into the tissue of the malar fat pad 20.

While the invention has been described with respect to certain embodiments, the description is intended to be illuminating, rather than limiting. Modifications and changes may be made within the scope of the invention, which is defined by the appended claims.

What is claimed is:

1. A malar implant, comprising:
   a superior edge shaped and adapted to be positioned on or around an inferior orbital rim of a human skull, the superior edge having a depending lip or tab that is angled with respect to the superior edge and is constructed and adapted to be secured to or on the inferior orbital rim, the depending lip or tab having one or more holes sized to admit fasteners for securing the malar implant to the inferior orbital rim;
   an inferior edge spaced generally vertically from the superior edge, and medial and lateral edges contiguous with the inferior and superior edges, the medial and lateral edges being spaced generally horizontally from one another;
   a central plateau arising between the superior, inferior, medial, and lateral edges, the central plateau extending outwardly from the superior, inferior, medial, and lateral edges to provide additional volume to underlying bone; and
   a plurality of soft tissue spikes positioned and arranged on the central plateau, the soft tissue spikes being adapted to attach to and support soft tissue in a selected position;
   wherein the malar implant is generally rigid.

2. The malar implant of claim 1, wherein the soft tissue spikes of the plurality of soft tissue spikes are hooked, with each spike tip making a first tip angle with respect to a central axis of the soft tissue spike in the range of about 80-120°.

3. The malar implant of claim 2, wherein the first tip angle is about 90°.

4. The malar implant of claim 2, wherein the central axes of the soft tissue spikes are inclined toward the superior edge at a second angle, taken with respect to a normal to the central plateau, in the range of about 45-65°.

5. The malar implant of claim 4, wherein the soft tissue spikes have the general shapes of isosceles triangular pyramids.

6. The malar implant of claim 1, wherein the soft tissue spikes have the general shapes of hooked or bent isosceles triangular pyramids.

7. The malar implant of claim 1, wherein the plurality of soft tissue spikes is arranged in rows on the central plateau.

8. The malar implant of claim 1, wherein the central plateau is curved outwardly.

9. The malar implant of claim 1, wherein the malar implant is formed of a biocompatible material.

10. The malar implant of claim 9, wherein the biocompatible material comprises a porous, high-density polyethylene.

11. The malar implant of claim 1, wherein at least a portion of the malar implant is formed of a resorbable biocompatible material.

12. A method of installing a malar implant to provide volume and lift to mid-face tissues, comprising:
    inserting the malar implant beneath the skin and soft tissues of a mid-face, the malar implant being made of a generally rigid material and having
        a superior edge shaped and adapted to be positioned on or around an inferior orbital rim of a human skull, the superior edge having a depending lip or tab that is angled with respect to the superior edge and is constructed and adapted to be secured to the inferior orbital rim, the depending lip or tab having one or more holes,
        an inferior edge spaced generally vertically from the superior edge, and medial and lateral edges contiguous with the inferior and superior edges, the medial and lateral edges being spaced horizontally from one another,
        a central plateau arising between the superior, inferior, medial, and lateral edges, the central plateau extending outwardly from the superior, inferior, medial, and lateral edges to provide additional volume to underlying bone, and
        a plurality of soft tissue spikes arising from the central plateau and being arranged on the central plateau, the soft tissue spikes being adapted to attach to and support soft tissue in a selected position;
    securing the lip or tab to the inferior orbital rim using one or more fasteners inserted through the one or more holes;
    selecting a vertical position for the soft tissues of the mid-face, the vertical position at least partially coinciding with the central plateau of the malar implant and one or more of the plurality of soft tissue spikes; and
    engaging the soft tissues of the mid-face on one or more of the plurality of soft tissue spikes.

13. A malar implant, comprising:
    a superior edge shaped and adapted to be positioned on or around an inferior orbital rim of a human skull, the superior edge having a depending lip or tab that is angled with respect to the superior edge and is constructed and adapted to be secured to or on the inferior orbital rim;
    an inferior edge spaced generally vertically from the superior edge, and medial and lateral edges contiguous with the inferior and superior edges, the medial and lateral edges being spaced generally horizontally from one another;
    a central plateau arising between the superior, inferior, medial, and lateral edges, the central plateau extending outwardly from the superior, inferior, medial, and lateral edges to provide additional volume to underlying bone; and
    a plurality of soft tissue spikes positioned and arranged on the central plateau, the soft tissue spikes being adapted to attach to and support soft tissue in a selected position;
    wherein the malar implant is made of a non-compliant material and the depending lip or tab extends generally perpendicular to the central plateau.

14. The malar implant of claim 13, wherein the depending lip or tab has one or more holes sized to admit fasteners for securing the malar implant to the inferior orbital rim.

* * * * *